United States Patent [19]

Sitrin et al.

[11] Patent Number: 5,102,989
[45] Date of Patent: Apr. 7, 1992

[54] METHOD OF STABILIZING RECOMBINANT HEPATITIS B VIRUS SURFACE PROTEINS FROM RECOMBINANT HOST CELLS

[75] Inventors: Robert D. Sitrin, Lafayette Hill; Dennis J. Kubek, Harleysville, both of Pa.

[73] Assignee: Merck & Co., Inc., Rahway, N.J.

[21] Appl. No.: 669,705

[22] Filed: Mar. 15, 1991

[51] Int. Cl.$^5$ .................... A61K 39/29; C07K 3/18; C07K 3/28

[52] U.S. Cl. ..................... 530/371; 424/89; 530/324; 530/412; 530/414; 530/417; 530/820; 530/825; 530/826; 530/824

[58] Field of Search ............ 424/89, 69.3; 530/324, 530/371, 412, 414, 417, 820, 824, 825, 826

[56] References Cited

U.S. PATENT DOCUMENTS

| | | | |
|---|---|---|---|
| 4,565,697 | 1/1986 | Ohmura et al. | 424/89 |
| 4,649,192 | 3/1987 | Van Wijnendaele et al. | 530/371 |
| 4,707,542 | 11/1987 | Friedman et al. | 530/371 |
| 4,738,926 | 4/1988 | Hamada et al. | 530/417 |
| 4,816,564 | 3/1989 | Ellis et al. | 520/324 X |
| 4,857,317 | 8/1989 | Wijnendaele et al. | 530/371 X |
| 4,992,531 | 2/1991 | Patroni et al. | 530/412 X |
| 5,011,915 | 4/1991 | Yamazaki | 424/89 X |

OTHER PUBLICATIONS

D. Wampler, et al., *Multiple Chemical Forms of Hepatitis B Surface Antigen*, P.N.A.S. U.S.A., 82, pp. 6830-6834 (1985).

P. Kniskern, et al., *A Candidate Vaccine for Hepatitis B Containing The Complete Viral Surface Protein*, Hepatology, 8, pp. 82-87, (1988).

R. Ellis, et al., *The Yeast Saccharomyces cerevisiae As a Host For Current and Potential Future Generation Recombinant-Derived Hepatitis B Vaccines*, in "Technological Advances In Vaccine, Development", pp. 127-136, (1988), Alan R. Liss, Inc.

*Primary Examiner*—Howard E. Schain
*Attorney, Agent, or Firm*—Hesna J. Pfeiffer

[57] ABSTRACT

Recombinant hepatitis B virus surface proteins produced in recombinant host cells are rapidly and efficiently purified from either cell extracts in a high pH buffer, or from heated whole cells at neutral pH. The host cell extracts or whole cells are heat treated, cooled and in the case of high pH extract, the pH is reduced. The surface proteins are then absorbed onto wide pore silica followed by elution and concentration. This method eliminates the requisite introduction of protease inhibitors, stabilizes the surface protein and improves product yield.

20 Claims, No Drawings

METHOD OF STABILIZING RECOMBINANT HEPATITIS B VIRUS SURFACE PROTEINS FROM RECOMBINANT HOST CELLS

BACKGROUND OF THE INVENTION

Hepatitis B virus (HBV) DNA contains several open reading frames, one of which is the env gene. This gene codes for 3 closely related proteins; preS1+preS2+S, preS2+S and S, in their respective 5'-3' genetic order and which comprise the structural envelope, or surface ("S") proteins. Collectively, the PreS1+PreS2+S, PreS2+S, and S proteins are referred to as hepatitis B virus surface proteins. The preS2+S and S proteins are capable of assembling into a structure known as the 22 nanometer (22 nm) particle or Australia antigen. The 22 nm particles can consist of a heterogeneous combination of S proteins or homogeneously of one form of S protein. All of the S related proteins are found in the intact HBV virion.

Through the use of recombinant DNA technology it has been demonstrated that the DNA coding for the S proteins can be introduced into various host cells (e.g. *E. Coli*, yeast, insect and mammalian cell cultures) resulting in the synthesis of preS1+preS2+S, preS2+S and S proteins, and the subsequent formation of 22 nm particles from preS2+S and S proteins. All three forms of the S protein are known to be immunogenic in vivo and antibodies to the S proteins are protective, with the preS2+S protein being immunodominant by virtue of the preS2 region. The preS2 region may function as a cellular membrane interaction sequence during the course of virus replication.

Expression of the preS2+S protein in yeast cells has demonstrated that the preS2+S protein interacts with yeast cell membranes and that purification of the preS2+S protein can be facilitated by this property.

Currently, a method exists for the purification of substantially pure membrane bound preS2+S protein. This method has several drawbacks which include: a) substantial amounts of contaminating yeast proteins at early stages of the purification scheme, b) proteolytic degradation of the preS2+S protein due to high levels of contaminating yeast proteases, c) the addition (and subsequent removal) of protease inhibitors to combat proteolytic degradation of preS2+S protein and, d) product yield reduction due to the culmination of the above factors. In addition, this protein, so purified, is being used as a vaccine in humans for the prevention of HBV infection.

It cannot be predicted what methods of purification will be useful for recombinant proteins since recombinant proteins are presented in a form which is usually atypical of the natural or classical form. For this reason, recombinant proteins frequently require novel combinations of known procedures or entirely new methods of purification.

In addition, vaccine preparations for human use require extreme purity which introduces even greater unpredictability in the outcome of a purification scheme.

OBJECTS OF THE INVENTION

It is an object of the present invention to provide a method for substantially purifying recombinant hepatitis B virus surface proteins from recombinant host cells. Another object of this invention is to provide a method of hepatitis B virus surface protein purification which eliminates the requirement of introducing protease inhibitors during purification. Another object of this invention is to provide a method for purifying recombinant hepatitis B virus surface protein from recombinant host cells resulting in a more stable surface protein product. These and other objects of this invention will be apparent from the following description.

SUMMARY OF THE INVENTION

This invention provides a method for the purification of recombinant hepatitis B virus surface proteins from recombinant host cells comprising the steps of:
   a) disruption of host cells expressing the recombinant surface protein in a high pH buffer yielding a crude extract;
   b) heat treating the crude cell extract (a);
   c) removing debris from the heat treated crude extract (b) in the presence or absence of detergent by: i) centrifugation or ii) microfiltration, yielding a heat treated clarified extract;
   d) concentration and diafiltration of the heat treated extract (c);
   e) reducing the alkalinity of the heat treated clarified extract (d);
   f) separating contaminating host cell proteins from the surface protein by contacting the product of step (d) with wide pore silica which adsorbs and retains the surface proteins but not contaminant proteins;
   g) elution of the adsorbed surface protein from the wide pore silica;
   h) subjecting the eluate of step (g) to diafiltration to further remove low molecular weight impurities and concentrate the final product yielding a substantially purified surface protein.

Alternatively, this invention also provides a method for this purification of recombinant hepatitis B virus surface proteins from recombinant host cells comprising the steps of:
   a) heat treating whole cells expressing the recombinant surface protein in a neutral pH buffer;
   b) disrupting the heat treated cells (a) yielding a crude extract;
   c) removing debris from the heat treated extract (b) in the presence of detergent by: i) centrifugation, or ii) microfiltration, yielding a heat treated clarified extract;
   d) concentration and diafiltration of the heat treated extract (c);
   e) removing the added detergent and separating contaminating host cell proteins from the surface protein by contacting the product of step (d) with a resin which adsorbs detergent, followed by contact with wide pore silica which adsorbs and retains the surface proteins but not contaminating proteins;
   f) elution of the adsorbed surface protein from the wide pore silica;
   g) subjecting the eluate of (f) to diafiltration to further remove low molecular weight impurities and concentrate the final product yielding a substantially purified surface protein.

DETAILED DESCRIPTION OF THE INVENTION

The processes of the present invention involve methods of purifying recombinant hepatitis B virus surface proteins from recombinant host cell extracts. These methods involve the combined treatment of host cell extracts with high temperature and elevated pH, or the treatment of whole cells at neutral pH and high temperature.

It will be understood that the novel purification processes of the present invention are applicable to a wide range of hepatitis B virus surface proteins or portions thereof, including S, preS1+preS2+S, and preS2+S proteins, whether the protein is derived from human or animal serum, or recombinant organisms. It will also be understood that various recombinant host cell species are encompassed by the method of this invention. Collectively, the preS1+preS2+S, preS2+S, and S proteins are referred to as hepatitis B virus surface proteins. Also included are fusion proteins containing all or portions of S, preS1+preS2+S, and preS2+S as well as multiple forms of hepatitis B virus surface proteins produced simultaneously in a recombinant host cell.

One principal example is recombinant preS2+S protein produced by yeast cells. This yeast expression system produces preS2+S amino acid sequences. Another example is recombinant S protein produced by yeast cells. Processes for the purification of other variant amino acid sequences of the S protein are encompassed by the present invention. The processes of the present invention are designed to provide rapid and efficient methods of purifying any S protein or S-fusion protein, including S protein variants as well as preS1+preS2+S and preS2+S variants and their respective fusion proteins, in accordance with the principals of the present invention. For example, conservative substitutions [defined as sets in Table 1 of Taylor, W. R., J. Mol. Biol. 188: 233 (1986)] in the preS1+preS2+S amino acid sequence generally will not result in any substantial or novel modification of the principals and practice of the present invention. Conservative substitutions of S antigen are known; see Elfassi, E. et al., J. Theor. Biol. 121: 371 (1986). In addition, deletions within the S, preS1 or preS2+S regions will not, in general, require any modifications of the processes for purification discussed herein. It will be understood that recombinant S Protein or surface antigen or recombinant preS1+preS2+S protein or preS2+S protein or portions thereof, in this application includes any such variations in the amino acid sequence, whether by conservative amino acid substitution, deletion or other process, provided that the recombinant S protein, the surface antigen, the recombinant preS1+S2+S protein or portions thereof, is immunochemically reactive with antibodies specific for the preS1+S2+S protein or portions thereof, the 22 nm particle, Australia antigen or other natural form of the HBV surface antigen sequence.

Many yeast based expression systems are clearly adequate for providing sources of recombinant preS2+S, S, and S-related proteins. The expression system of *Saccharomyces cerevisiae* is intended as an incidental source. Other yeast vectors include but are not limited to shuttle vectors, cosmid plasmids, chimeric plasmids and those having sequences derived from 2 micron circle plasmids.

The genus Saccharomyces is composed of a variety of species. Most commonly used is *S. cerevisiae*, or baker's yeast, as a host for recombinant DNA-mediated expression of a variety of foreign polypeptides. However, the destinction between other species of the Saccharomyces genus are not always well defined. Many of these species are capable of crossmating with *S. cerevisiae* and are likely to possess regulatable promoters and other transcriptional and translational regulatory elements which are analagous or identical to those in *S. cerevisiae*. Therefore, it will be obvious to those skilled in the art that for expression of S-related polypeptides, the selection of a host extends to other species of the genus Saccharomyces including but not limited to carlsbergensis, uvarum, rouxii, montanus, kluyveri, elongrgsorus, norbensis, oviformis and diastaticus.

Dane particles (serotype adw) were utilized as the source of HBV nucleic acid for the isolation of the viral open reading frames (ORF). It is obvious to those skilled in the art that this procedure extends to the use of nucleic acid from HBV strains with other serologic reactivities which derive from viral genetic diversity. The endogenous polymerase reaction was employed in order to produce covalently-closed circular double-stranded DNA of the HBV genome from the nicked and gapped nucleic acid form that natively resides in the HB virion. The DNA was isolated, digested to completion with EcoRI, and cloned into the EcoRI site of pBR322, thus generating pHBV/ADW-1. The recombinant plasmids containing the HBV genome in a circularly permuted form at the EcoRI site of the PreS region were selected. The complete ORF encoding the 55 amino acids (aa) of the preS2 region and the 226 aa of the S region was constructed first by purifying the 0.8 kilobase pair (kbp) fragment obtained following digestion of pHBV/ADW-1 with EcoRI and AccI; this fragment encodes the PreS2+S polypeptide lacking only the initiation codon, the amino-terminal 3 aa, the carboxy-terminal 3 aa, and the translational terminator codon.

Oligonucleotides were synthesized and ligated to this fragment, converting it to a HindIII fragment containing a 10 bp yeast-derived non-translated 5' flanking sequence and the complete preS2+S ORF. The sequence at the 3' flank of the preS2+S ORF was chosen such that the termination codon directly abutted a natural HindIII site in the ADHI transcriptional terminator, thus creating a completely native yeast-derived junction without any additional intervening bases. It is obvious to those skilled in the art that for expression of preS2+S, any suitable yeast-active transcriptional terminator may be substituted for ADHI.

The 5' flanking sequence for the construction (ACAAAACAAAA) was chosen to correspond to that for the non-translated leader (NTL) of the yeast gene GAP63 (GAP) [Holland, *J. Biol. Chem.*, 225, 2596 (1980)] and is also a consensus for the GAP gene family. The construction was made in such a manner as to abut the NTL directly to the initiation codon of the preS2+S ORF without the intervention of any additional bases. Therefore, it is obvious to those skilled in the art that, for expression of envelope polypeptides, the selection of NTL sequences extends to other sequences which result in suitable expression levels.

DNA sequence analysis revealed 2 base substitutions which resulted in aa differences from the preS2+S sequence encoded by the DNA of pHBpreS-GAP347/19T [Valenzuela et al., *Biotechnology*, 3(4), 317–320 (1985)]. In order to evaluate identical polypeptides for both constructions, these nucleotide substitutions, which were T instead of C at base 64 of the 846 bp ORF of HBV preS2+S (encoding Phe rather than Leu) and C instead of A at base 352 (encoding His rather than Gln) were changed by site-directed mutagenesis [Zoller et al., *Nucleic Acids Research* 10:6487–6500 (1982)]. The encoded aa sequence for the optimized construction then was verified. It is obvious to those skilled in the art that this invention is not limited to this sequence and extends to any sequence wherein the DNA encodes a polypeptide with HBV antigenicity.

Following mutagenesis, the fragment described above was used to construct an expression cassette, as described previously [Kniskern et al., *Gene*, 46:135–141, (1986)], which was composed of: (a) ca. 1.1 kbp of the GAP491 promoter, (b) a 10 bp yeast-derived flanking sequence, (c) 846 base pairs of the HBV preS2+S gene (serotype adw) lacking any viral flanking sequences, and (d) ca. 0.4 kbp of the yeast ADH1 terminator. This expression cassette was inserted into the yeast shuttle vector pC1/1 [Beggs, *Nature.* 275:104, (1978); Rosenberg et al., *Nature,* 312:77, (1984)] to create plasmid pYGpreS2S-1 which was used to transform yeast strain CF42, generating a transformant hereafter called pF403. This transformant was established as a frozen stock for evaluation and subsequent experimentation. Parental strain CF42 was obtained as follows: a spontaneous ura3 mutation in yeast strain 2150-2-3 (L. Hartwell, U. of Washington) was selected [Boeke et al., *Mol. Gen. Genet.,* 197:345–346, (1984)]. The resulting strain (MATa, ade1−, leu2-04−, ura3−, cir°) was diploidized by transforming with plasmid YCp50-HO [Jensen et al., *P.N.A.S. U.S.A.,* 80:3035–3039, (1983)]. The functional yeast gene HO allows cells to switch mating type. Thus, progeny from single cell transformants will be a mixture of both a and a mating types and will mate during colony growth. A diploid clonal isolate was cured of the plasmid and designated CF42 (MATa/a, ade1−, leu2-04−, ura3−). These transformants were established as frozen stocks for evaluation and subsequent experimentation.

Recombinant yeast from the pF403 frozen stocks was grown in YEHD medium [Carty et al., *J. Industrial Micro.,* 2, 117–121, (1987)]. After growth to stationary phase, yeast cells were harvested. Lysates were prepared, resolved by sodium dodecylsulfate-polyacrylamide gel electrophoresis (SDS-PAGE), and immunoblotted with antibodies to HBsAg. Two major polypeptides were found with molecular weights of about 30 kD and 34 kD in accord with the predicted molecular weight of the translational product of the preS2+S ORF and its glycosylated derivative. An additional polydisperse (molecular weight of about 50 kD) glycopeptide band also was detected which corresponded to the population of hyperglycosylated species and which was immunoreactive with anti-yeast as well as anti-HBs sera. Furthermore, lysates of recombinant, but not parental, yeast were positive for preS2+S by radioimmunoassay (RIA). Electron microscopic examination of partially purified yeast lysates showed high densities of typical 22 nm preS2+S particles.

The yeast-derived promoter initiates transcription of the preS2+S gene. Therefore, it is readily apparent to those skilled in the art that any yeast-active promoter sequence may be substituted for the GAP491 promoter. It is also readily apparent to those skilled in the art that a suitable assay system, e.g., immunoblot or RIA or enzyme-linked immunoassay (EIA), should be utilized in order to assay expression of preS2+S polypeptides in this system, such that the time of harvesting of the culture for attaining a maximal yield can be optimized.

The GAP491 promoter has been useful for the expression in yeast of several foreign proteins, including HBsAg [Bitter et al., *Gene,* 32:263–274, (1984); Wampler et al., *Proc. Nat. Acad. Sci. U.S.A.,* 82:6830–6834, (1985)]. Based upon our previous results of expressing HBcAg to ca. 40% of soluble yeast protein (Kniskern et al., supra), we have used this promoter to drive the expression of preS2+S antigen in suitable yeast host cells.

In order to control and define the glycosylation of recombinant yeast-expressed preS2+S protein, the yeast expression plasmid (pYGpreS2S-1) containing the expression cassette described above also was used to transform *S. cerevisiae* strain KHY-107 (cir+, ade1+, leu2−, mnn9−) which was constructed as follows:

An a mating type strain CZ5/LB347-1C (mnn 9−, SUCZ−) (C. Ballou, U. of Calif.) was mated with the a type strain 2150-2-3 (leu2−, ade1−) (L. Hartwell, U. of Washington) by mixing the strains on a YEHD agar plate (Carty et al., supra). To select for diploids, the mated strains were replica-plated onto minimal media without leucine (leu−) and containing 2% sucrose as the sole carbon source. After isolating single colonies, the diploids were sporulated, and asci were dissected by standard techniques. The KHY-107 strain was isolated as a single spore and characterized as cir+, ade1+, leu2−, and mnn9− (by Schiff stain technique).

Transformed clones were selected on minimal medium (leu−) containing 1M sorbitol. These cloned transformants were established as frozen stocks in 17% glycerol for subsequent evaluation and further experimentation.

The expression plasmid pYGpreS2S-1 also was used to transform KHY-107 (cir°, ade1+, leu2−, mnn9−), which was derived from strain KHY-107 (cir+, ade1+, leu2−, mnn9−) as described (Broach, G. R. "Methods in Enzymology", Vol. 101, part C, pg 307–325, 1987, Academic Press, N.Y.). Transformed clonal isolates were established as frozen stocks in 17% glycerol for subsequent evaluation and further experimentation.

Clones of transformed yeast [KHY-107(cir+, ade1+, leu2−, mnn9−)] containing the expression plasmid pYGpreS2S-1 were plated onto leu− selective agar plates containing 1M sorbitol and incubated at 30° C. for 2 to 3 days. These yeast were inoculated into 5 to 7 mL cultures of complex YEHD (Carty et al., supra) medium containing 1M sorbitol, and the cultures were incubated at 30° C. with aeration for 12 to 18 hrs. Flasks containing 50 mL complex YEHD media with 1M sorbitol (hereafter called YEHDS) were inoculated from the above cultures (to an initial $A_{600}$ of about 0.1) and were incubated at 30° C. with shaking (350 rpm) for 48–72 hrs to a final $A_{600}$ of 10–16. Samples of 10 $A_{600}$ units were aliquoted into tubes, and the yeast cells were pelleted at 2000 xg for 10 minutes. Samples either were assayed directly or stored frozen at −70° C. At the time of assay, the pellets were resuspended in 0.4 mL of phosphate-buffered saline (PBS) containing 2 mM phenylmethyl sulfonyl fluoride (PMSF) and transferred to 1.5 mL Eppendorf tubes. Yeast cells were broken by: 1) the addition of 200–300 mg of washed glass beads (0.45 mm) and agitation on a vortex mixer for 15 min, 2) addition of TRITON X-100 to 0.5%, 3) agitation on the vortex mixer for 2 minutes, and 4) incubation at 4° C. for 10 minutes. Cellular debris and glass beads were removed by centrifugation at 2000 xg for 10 minutes. The clarified supernatant fluid was removed and assayed for protein [by the method of Lowry et al., *J. Biol. Chem.,* 193, 265, (1951)] and RIA specific for preS2+S [Hansson et al., *Infect. Immunol.* 26: 125–130, (1979), Machida et al., *Gastroenterology* 86: 910–918, (1984)].

Five clones were evaluated in parallel and compared to an equivalent cell pellet from clone pF403 which was normalized to a value of 1.0 for reference. Typical relative values of antigen productivity for the five clones were obtained as listed in Example VII.

Clones of transformed yeast [KHY-107 (cir°, ade1+, leu2−, mnn9−)] containing the expression plasmid were plated onto leu− selective agar plates containing 1M sorbitol and incubated at 30° C. for 2 to 3 days. These yeast were inoculated into 5 to 7 mL cultures of complex YEHDS media, and the cultures were incubated at 30° C. with aeration for 12 to 18 hrs. Flasks containing 50 mL complex YEHDS media were inoculated from the above cultures (to an initial $A_{600}$ of 0.1) and were incubated at 30° C. with shaking (350 rpm) for 48 to 72 hrs to a final $A_{600}$ of 10 to 16. Triplicate samples of 10 $A_{600}$ units were aliquoted into tubes, and the yeast cells were pelleted at 2000 xg for 10 min. Samples either were assayed directly as described above or stored frozen at −70° C.

Five clones were evaluated in parallel and compared to clone pF403 which was normalized to a value of 1.0 for reference. Typical relative values of antigen productivity for the five clones were obtained as listed in Example VIII.

Immunoblot analysis of the preS2+S polypeptide derived from all recombinant clones described above, in host cells with the mnn9 phenotype, showed two bands with apparent molecular sizes of 30 kD and 34 kD. The polydisperse (molecular weight greater than 50 kD) hyperglycosylated species were not detected with either anti-yeast or anti-HBs sera.

In order to provide for an expression vector in which the intrinsic nature of the expressed protein defines the control of glycosylation of the HBV preS2+S, the recognition sequence for N-linked glycosylation [Asn-X-Thr] within the preS2+S ORF was mutated. The clone PUC13PreS2S served as the starting material for this construction.

To reconstruct the 5′ portion of the preS2+S ORF, a pair of oligonucleotides was synthesized to reconstitute the ORF from BamHI upstream to the ATG through a 10 bp NTL and a HindIII site to an EcoRI compatible terminus. The sequence of this oligonucleotide, which contains an A to C mutation (at base 31) and a T to A mutation (at base 33) and which would result in an aa change at position 4 of the S2 Protein domain from Asn to Gln, is:

AAT TCA AGC TTA CAA AAC AAA ATG CAG TGG CAA TCC
    GT TCG AAT GTT TTG TTT TAC GTC ACC GTT AGG

ACT GCC TTC CAC CAA GCT CTG CAG
TGA CGG AAG GTG GTT CGA GAC GTC CTAG

This synthetic oligonucleotide pair was ligated into pUC19 which had been digested previously with EcoRI and BamHI. The resultant plasmid was digested with BamHI and SalI and subsequently ligated with the 0.8 kbp BamHI to SalI fragment digested and purified from pUC13preS2S to create the plasmid PUC19-preS2SWG-1 which, as a HibdIII fragment, contains the preS2+S ORF with Gln substituted for Asn at positon 4. This ORF was used to create a yeast expression vector in an analogous fashion as described earlier.

In an analogous fashion the 0.8 kbp HindIII fragment was isolated from pUC13preS2S and ligated into a pUC19 vector in which the EcoRI and BamHI sites had been previously destroyed. The resultant vector was digested with EcoRI and BamHI and ligated with a pair of synthetic oligonucleotides which was designed to recreate the preS2+S envelope ORF from EcoRI to BamHI with an A to G mutation (at base +7 of the oligonucleotide) which results in an amino acid interchange from Thr to Ala at amino acid +6 of the preS2 domain.

The sequence of this oligonucleotide is:

ATT TCC GCT GCC TTC CAC CAA GCT CTG CAA
    GG CGA CGG AAG GTG GTT CGA GAC GTT CTAG

This construction resulted in the creation of pUC19-preS2SWG-2 which contains the ORF as a HindIII fragment with Ala substituted for Thr at amino acid 6 of the preS2 domain. This ORF was used to create a yeast expression vector in an analogous fashion as described earlier.

PreS2+S antigen expression was evaluated as described previously and was shown to be equivalent in productivity to that obtained with transformants described above. Clones of both mutants were preserved as frozen stocks for further evaluation. Immunoblot analysis developed with either anti-HBs sera or anti-preS2 sera detected a single major species with a molecular weight of about 30 kD which is consistent with that predicted for the non-glycosylated translation product of the preS2+S ORF.

For in vivo potency determinations, the nonhyperglycosylated preS2+S preparation was adsorbed to alum, and groups of mice were injected with graded quantities of antigen. After six weeks, the mouse sera were assayed for anti-HBs antibody (AUSAB*) and anti-preS2 antibody [according to Neurath, *J. Med. Virol.*, 17, 119–121, (1985)]. The results of such experiments indicated that the preS2+S preparation was equally as effective as the HBsAg control preparation in inducing an anti-HBs antibody response (the effective immunizing dose was 0.34 mg for preS2+S as compared to 0.25 mg for the HBsAg control). In addition, the preS2+S preparation demonstrated a potent (effective immunizing dose of 0.14 mg) ability to induce a concomitant antibody response specific for the preS2 domain.

The genus Saccharomyces is composed of a variety of species. Most commonly used is *S. cerevisiae*, or baker's yeast, as a host for recombinant DNA-mediated expression of a variety of foreign polypeptides. However, the destinction between other species of the Saccharomyces genus are not always well defined. Many of these species are capable of crossmating with *S. cerevisiae* and are likely to possess regulatable promoters and other transcriptional and translational regulatory elements which are analagous or identical to those in *S. cerevisiae*. Therefore, it will be readily apparent to those skilled in the art that for expression of S-related polypeptides, the selection of a host extends to other species of the genus Saccharomyces including but not limited to carlsbergensis, uvarum, rouxii, montanus, kluyveri, elongrgsorus, norbensis, oviformis and diastaticus.

Several yeast genera such as Hansenula, Candida, Torulopsis and Pichia have been shown to contain metabolic pathways for the utilization of methanol as the sole carbon source for growth. The gene for alcohol oxidase, an enzyme which participates in this metabolic pathway has been isolated from *Pichia pastoris*. The *P. pastoris* alcohol oxidase gene promoter has been isolated and shown to be inducible in the presence of methanol. Such an inducible promoter system is useful for the expression of polypeptides which have a negative effect on the host. In particular, this promoter has been shown to be active in regulating the expression of S polypeptides in *P. pastoris* highlighting the ability of other yeast genera to function as hosts for the recombinant DNA-mediated gene expression of S polypeptides in immunologically active form. Therefore it will be obvious to those skilled in the art that, for the expression of preS2+S containing polypeptides the selection of a host extends to species from other genera of yeast from the Families Saccharomycetaceae and Cryptococcaceae, including, but not limited to Pichia, Candida, Hansenula, Torulopsis, Kluyveromyces and Saccharomycopsis.

The methods of purification of recombinant preS2+S of this invention completely eliminate the formerly requisite introduction of protease inhibitors in any of the purification steps. Yeast cells transformed with expression vectors coding for a hepatitis B virus surface protein or variants thereof are grown and harvested. The cells may be stored if desired by washing the cells in a buffer solution, e.g. PBS, and forming a cell paste which is typically stored frozen at −70° C.

Purification typically begins as follows. A batch of fresh or frozen cell paste is suspended in a buffer, preferably TRIS, at a high pH ranging between about 8.5 and about 11.0, preferably about 10.5. The cells are then disrupted, preferably by mechanical means. The gentle bead breakage method of disruption has been found to be unsuitable for scale-up use. Disruption by a high pressure homogenizer (about 10,000 to 20,000 psi, using a Gaulin or Stansted homogenizer) is preferred because of its rapid and efficient operation.

Disruption of the yeast cells results in a crude extract. The crude extract is then pH adjusted. The pH is adjusted to within the range of 8.0 to 11.0, with 10.5 being preferred.

It may be desired at this point to add a detergent to the crude extract. The addition of a detergent will facilitate the separation of yeast cell membranes from unwanted cellular debris. It has been shown that preS2+S protein, as well as other forms of the surface proteins, associate with yeast cell membranes. A variety of neutral or non-ionic detergents can be used, including but not limited to detergents of the TRITON-N series, TRITON-X series, BRIJ series, TWEEN series or EMASOL series, deoxycholate, octylglucopyranoside or NONIDET-Np-40. Zwitterionic detergents such as CHAPS or CHAPSO are also useful and suitable agents.

If a detergent is to be used, the preferred detergent is TRITON X-100 at a concentration of about 0.5%. It must be stressed that the method of this invention does not require detergent use at this step and the use of detergents is optional.

The extract is then heat treated. Heat treatment is effective over a range of temperatures and for a range of treatment duration. Typically a temperature range of 45° C. to 60° C. is used, with 50° C. as the preferred temperature. The duration of heat treatment typically ranges between 20 to 40 minutes with 30 minutes as the preferred time. The extract is heat treated in a suitable vessel and the vessel is immersed in a heated bath, or a heat exchanger is used. The material is then cooled to about 10° C., preferably by placing it into an ice-water bath or by using a heat exchanger. It will be readily apparent to those skilled in the art that, according to the method of this invention, the order in which the heat treatment and the debris removal steps are done may be reversed without significant effect on the result of this procedure. Alternatively, whole yeast cells can be heated in a neutral pH buffer, disrupted and detergent added as described above.

Removal of cellular debris from the heat treated crude extract is necessary to prevent physical occlusion during subsequent purification steps. Debris can be removed by centrifugation, microfiltration, or filtration producing a clarified extract. Centrifugation and microfiltration are the most preferred methods. Centrifugation can be done for varying lengths of time at different centrifugal force. Centrifugation at about 3,000×g for 15 minutes at 4° C. has been found adequate. It may also be advantageous to dilute the extract before centrifugation to reduce the typically viscous nature of a crude yeast cell extract. Dilution will not alter any subsequent steps of this procedure.

Microfiltration has an advantage in that filtration and dialysis can be performed simultaneously. Several types of microfiltration units are suitable for use in this step, e.g. KROSFLO by Microgon Inc. or any variety of hollow fiber cartidges by Amicon or A/G Technology. The preferred microfiltration method is to pass the extract through Prostak Durapore (Millipore) membrane, plate and frame microfiltration unit with a pore size of about 0.1 microns to 0.2 microns, at an inlet pressure of about 2 to 7 psi, using a buffer consisting of about 0.1M TRIS, pH about 10.4 and about 0.1% TRITON X-100.

The supernatant from centrifugation or the filtrate from microfiltration may be concentrated prior to the next step of this procedure. Concentration can be achieved by several methods including, but not limited to, dialysis, filtration, lyophilization, ultrafiltration and diafiltration. The preferred method of concentration of the present invention is to run the clarified extract through a $10^5$ molecular weight cut off, hollow fiber ultrafiltration system. The volume of the clarified extract is typically reduced by about 6.5 fold for the microfiltration product and about 2 fold for the diluted, centrifuged product, yielding a concentrated retentate. Following concentration, the retentate is diafiltered to further remove lower molecular weight contaminants. Diafiltration is performed using a $10^5$ molecular weight cutoff, hollow fiber system.

If TRITON X-100 was added, it can be removed by several conventional methods including, but not limitted to, dialysis, addition of certain organic solvents, refrigeration, chromatographic separation, and contact with a gel or resin which specifically binds detergents, such as Extractogel (Pierce) and XAD resin (Romicon). The preferred method of this invention to remove TRITON X-100 is to circulate the heat treated extract containing TRITON X-100 through a cartridge of XAD-2 or XAD-4 resin (polystyrene divinylbenzene). The heat treated extract is circulated through the XAD cartridge for about 10 hours at 4° C. and then collected in a suitable vessel, for example, a sealable glass bottle.

If the cells were disrupted in a high pH buffer, the pH of the heat treated extract is then adjusted to between about pH 7.0 to about 7.9 with the preferred pH of about 7.7. Adjusting the pH to about 7.7 following heat treatment at a high pH according to the method of this invention, greatly facilitates the adsorption of surface proteins to the wide pore silica utilized in a subsequent step. Adjustment of the pH of the heat treated extract can be performed prior to the Triton X-100 removal step without effecting the outcome of the procedure. Therefore, it will be obvious to those skilled in the art that, according to the method of this invention, the order in which the pH adjustment and the Triton X-100 removal steps are done may be reversed without significant effect on the result of this procedure.

The surface protein is then easily separated from the contaminants yielding substantially purified hepatitis B virus surface protein. The preferred method of eliminating the contaminants is to adsorb the surface protein onto wide pore silica. The most preferred method of this invention is to adsorb the surface protein onto a wide pore silica with a pore size range of about 1000 to 1500 angstroms and silica particle size range of about 30 to 130 microns (Amicon). The surface protein readily enters the pores of the silica and is retained. The yeast cellular protein contaminants can therefore be easily washed away.

Adsorption of surface protein onto wide pore silica can be done chromatographically or in a non-chromatographic, batchwise fashion. Chromatographic adsorption is done by passing the pH adjusted extract through a bed of wide pore silica in a column chromatography apparatus. Typically, about one liter of heat treated extract is applied to a 5 cm jacketted column apparatus containing about 300 ml (about 100 g dry weight) of wide pore silica beads at a flow rate of about 200ml/hour.

Non-chromatographic adsorption onto wide pore silica is typically done by mixing the heat treated extract with the silica in a suitable vessel, e.g. a sealable glass bottle. The preferred method is to add 300 ml of wide pore silica to about one liter of heat treated extract in a glass bottle and incubate with constant mixing. Adsorption preferably continues for about 1.5 hours at about 4°-8° C. although different times and temperatures are suitable.

Washing of the surface protein-adsorbed silica free of unadsorbed material can also be done non-chromatographically, or the silica can be poured into a column apparatus, as previously described, for chromatographic adsorption. Batchwise washing is done by draining the heat treated extract from the wide pore silica and adding several volumes of a buffer which will not cause the release of surface proteins adsorbed onto the silica. The preferred buffer is PBS. The silica is drained and the washing steps are repeated 3 to 5 times.

Chromatographic washing of the surface protein-adsorbed silica is done by passing PBS through the silica at a flow rate of about 200 ml/hour until the extinction at 280 nm is constant.

The surface protein is eluted from the washed wide pore silica using a buffer solution with a pH between about 8.5 to 9.0. Surface proteins are preferably desorbed using a buffer solution consisting of about 0.05M Borate at a pH of about 8.7. Desorption of surface proteins can be facilitated at elevated temperatures over a wide range. Desorption at about 55° C. is preferred.

Non-chromatographic desorption is done by mixing 1200 ml of 0.05M Borate buffer at pH 8.7 with about 700 ml of washed surface protein-adsorbed wide pore silica. Desorption continues for about 25 minutes. The eluate is then collected, the desorption steps are repeated twice and the eluate is cooled.

Chromatographic desorption is done by warming the jacketted column of washed silica to about 55° C. The 0.05M Borate buffer at pH 8.7 is warmed to 55° C. and then applied to the column at a rate of 500 ml/hour. The eluate is then collected and cooled. The volume of eluate is usually roughly equivalent to the volume of heat treated extract applied to the wide pore silica.

Concentration of the eluted surface protein is usually desired. The preferred concentration method is to pass the eluate through a $10^5$ molecular weight cut-off hollow fiber diafiltration system using a 0.05M Borate buffer, pH 8.7. The volume of the eluted surface protein may be generally reduced by as much as 16 fold using this system. The diafiltration retentate can be sterilized by microfiltration if necessary.

The following examples illustrate the present invention without, however, limiting the same thereto. The disclosure of each reference mentioned in the following examples is hereby incorporated by reference.

EXAMPLE I

Cloning of HBV DNA in pBR322

HBV Dane particles (serotype adw) were isolated and purified from human plasma (carrier), and double-stranded DNA was synthesized by the endogenous polymerase in the Dane particles according to the methods of Landers et al., [*J. Virology*, 23, 368–376, (1977)] and Hruska et al., [*J. Virology*, 21, (1977)]. The DNA was isolated after digestion with Proteinase K in SDS followed by extraction with phenol/chloroform and ethanol precipitation. The HBV genomic DNA was digested with EcoRI, producing a single 3.2 kbp fragment, that was cloned into the EcoRI site of pBR322 to form pHBV/ADW-1. The presence of the HBV DNA was confirmed by EcoRI digestion, Southern blot transfer to nitrocellulose, and hybridization with [$^{32}$P]-labelled specific oligonucleotide probes.

EXAMPLE II

Cloning of the preS2+S Gene into the pGAP-tADH-2 Expression Vector

Plasmid pHBV/ADW-1 (described in Example I) was digested with EcoRI and AccI, and the 0.8 kbp fragment purified by preparative agarose gel electrophoresis.

To reconstruct the 5' portion of the preS2+S ORF, a pair of oligonucleotides was synthesized which reconstitutes the ORF from the EcoRI site upstream to the ATG through a 10 bp NTL sequence to a HindIII terminus. The sequence of this oligonucleotide is:

```
AGCTTACAAAACAAAATGCAGTGG
    ATGTTTTGTTTTACGTCACCTTAA
```

To reconstitute the 3' portion of the preS2+S ORF, a second pair of oligonucleotides was synthesized which reconstitutes the ORF from the AccI site through the translational terminator to a HindIII terminus. The sequence of this oligonucleotide is:

ATACATTTAA
TGTAAATTTCGA

The plasmid pGAP-tADH-2 containing the GAP491 promoter [Holland et al., *J. Biol. Chem.*, 255:2596, (1980)] and the ADH1 transcriptional terminator in pBR322, has a unique HindIII cloning site into which the preS2+S ORF described above was ligated, yielding pEGpreS2S-1. The presence and orientation of HBV DNA was confirmed by restriction endonuclease analyses and Southern blot transfer. The expression cassette containing the preS2+S ORF was removed from pEGpreS2S-1 by SPhI digestion and isolated by preparative agarose gel electrophoresis. The cassette then was cloned into the shuttle vector pC1/1 (Beggs, supra; Rosenberg et al., supra) which had been digested previously with SphI to create a yeast expression vector (pYGpreS2S-1) which was then used to transform *S. cerevisiae* as described below.

EXAMPLE III

Transformation and Establishment of Seed Stocks for PreS2+S Expression in Yeast "Wild Type" for Glycosylation The resultant plasmid pYGpreS2S-1 (from Example II above) containing the expression cassette was used to transform *S. cerevisiae* strain CF42, (MATa/a, ade1−, leu2-04−, ura3−), which was created as follows:

A ura3 mutation in yeast strain 2150-2-3 (L. Hartwell, U. of Washington) was selected (Boeke et al., supra). The resulting strain (MATa, ade1−, leu2-04−, ura3−, cir°) was diploidized by transforming with the plasmid YCp50-HO [Jensen et al., PNAS U.S.A., 80: 3035–3039, (1983)]. A diploid strain was cured of the plasmid and designated CF42, (MATa/a, ade1−, leu2-04−, ura3−).

A transformed clone (pF403) was selected and established as a frozen stock (in 17% glycerol) for evaluation as described below.

EXAMPLE IV

Growth and Expression of the preS2+2 Gene in Yeast "Wild-type" for Glycosylation The clone pF403 of yeast containing the expression plasmid described in Example III was plated onto leu− agar plates and incubated at 30° C. for 2–3 days. These yeast were inoculated into 5–7 mL cultures of complex YEHD media, and the cultures were incubated at 30° C. with aeration for 12–18 hrs. Flasks containing 50 mL complex YEHD media were inoculated from the above cultures to an $A_{600}$ of 0.1 and were incubated at 30° C. with shaking (350 rpm) for 48–72 hrs to a final $A_{600}$ of 10–16. Triplicate samples of 10 $A_{600}$ units were aliquoted into tubes, and the yeast cells were pelleted at 2000 xg for 10 minutes. The pellets either were assayed directly or stored at −70° C. for future use as an internal reference standard for the evaluation of the controlled glycosylation clones described below in Examples VII, VIII, IX and X (for these comparisons, values for clone pF403 were normalized to 1.0). At the time of assay, the pellets were resuspended in 0.4 mL of phosphate-buffered saline containing 2 mM PMSF. Yeast cells were broken by: 1) the addition of 200–300 mg of washed glass beads (0.45 mm), 2) agitation on a vortex mixer for 15 min, 3) addition of TX-100 to 0.5% (v/v), 4) agitation on a vortex for 2 min, and 5) incubation at 4° C. for 10 min. Cellular debris and glass beads were removed by centrifugation at 2000 xg for 10 min. The clarified supernatant fluid was removed and assayed for protein [by the method of Lowry et al., *J. Biol. Chem.*, 193, 265 (1951)] and by an RIA specific for preS2+S [Hansson et al., supra. Machida et al., supra.].

EXAMPLE V

Yeast Transformation and Seed Establishment of PreS2+S in a Circle (+) mnn9 Mutant Yeast The resultant plasmid (pYGpreS2S-1) from Example II above containing the expression cassette was used to transform *S. cerevisiae* KHY-107 (cir+) which was constructed as follows:

The a mating type strain CZ5/LB347-1C (mnn 9−, SUCZ−) was mated with the a type strain 2150-2-3 (leu2−, ade1−) by mixing the strains on a YEHD complete media plate. To select for diploids, the mated strains were replica plated onto leu− minimal medium and containing 2% sucrose as the sole carbon source. After isolating single colonies, the diploids were sporulated, and asci were dissected by standard techniques. The KHY-107 strain was isolated as a single spore and characterized as cir+, ade1+, leu2−, and mnn9− (by Schiff stain technique).

Clones were selected on minimal medium (leu− and containing 1M sorbitol), established as frozen stocks (in 17% glycerol) and evaluated as described below.

EXAMPLE VI

Yeast Transformation and Seed Establishment for PreS2+S in a Cir° mnn9 Mutant Yeast The expression plasmid described in Example II above was used to transform *S. cerevisiae* strain KHY-107 (cir°) which was derived from strain KHY 107 (cir+) as described by Broach ["Methods in Enzymology", Vol 101, Part C. 307–325, (1983)]. Clones were selected, established as frozen stocks as described above in Example V, and evaluated for expression of preS2+S as described below in Example VIII.

EXAMPLE VII

Growth and Expression of the preS2+S Gene in Circle+mnn9 Mutant Yeast

Clones of yeast containing the expression plasmid described in Example V were plated onto leu− selective agar plates containing 1M sorbitol and incubated at 30° C. for 2–3 days. These yeast were inoculated into 5–7 mL cultures of complex YEHDS and the cultures were incubated at 30° C. with aeration for 12–18 hrs. Flasks containing 50 mL YEHDS media were inoculated from the above cultures (to an initial $A_{600}=0.1$) and were incubated at 30° C. with shaking (350 rpm) for 48–72 hrs at a final $A_{600}$ of 10–16. Samples of 10 $A_{600}$ units were aliquoted into tubes, and the yeast cells were pelleted at 2000 xg for 10 min. Samples either were assayed directly as described in Example IV or stored frozen at −70° C. Cellular debris and glass beads were removed by centrifugation at 2000 xg for 10 min. The clarified supernatant fluid was removed and assayed for protein and by an RIA specific for preS2+S, as described previously.

Five clones were evaluated in parallel and compared to an equivalent cell pellet from clone pF403 (see Example IV above) which was normalized to a value of 1.0 for reference. Typical relative values of antigen productivity for the five clones were:

| Clone | Relative[1]<br>mg preS2 + S/ml | Relative[1]<br>units PreS2 + S/<br>units Protein |
|---|---|---|
| a | 1.6 | 0.7 |
| b | 1.4 | 0.25 |
| c | 1.2 | 0.5 |
| d | 1.5 | 0.3 |
| e | 1.3 | 0.2 |
| pF403 | 1.0 | 1.0 |

[1]Ellis et al., (1987) In "Viral Hepatitis and Liver Disease" A. Zuckerman (ed), New York: Alan R. Liss Inc. p. 1079. and Kniskern, et al., (1988) Hepatology, 8, 82–87.

Immunoblot analysis developed with rabbit anti-HBs or McAb to the preS2 domain detected a single major species with a molecular weight of ca. 34-kD. Clone "a" above, hereinafter referred to as Clone 14007-230-1A, was selected for further development.

EXAMPLE VIII

Growth and Expression of the preS2+S Gene Cir° mnn9 Mutant Yeast

Clones of yeast containing the expression plasmid described in Example VI were plated onto leu⁻ selective agar plates containing 1M sorbitol and incubated at 30° C. for 2–3 days. These yeast were inoculated into 5–7 mL of YEHDS medium and the cultures were incubated at 30° C. with aeration for 12–18 hrs. Flasks containing 50 mL complex YEHDS medium were inoculated from the above cultures (to an initial $A_{600}=0.1$) and were incubated at 30° C. with shaking (350 rpm) for 48–72 hrs to a final $A_{600}$ of 10–16. Triplicate samples of 10 $A_{600}$ units were aliquoted into tubes, and the yeast cells were pelleted at 2000 xg for 10 min. Samples either were assayed directly as described previously or stored frozen at −70° C. Cellular debris and glass beads were removed by centrifugation at 2000 xg for 10 min. The clarified supernatant fluid was removed and assayed for protein and preS2+S antigen as described previously.

Five clones were evaluated in parallel and compared to clone pF403 (see Example IV above) which was normalized to a value of 1.0 for reference. Typical relative values of antigen productivity for the five clones were:

| Clone | Relative*<br>mg preS2 + S/ml | Relative*<br>units PreS2 + S/<br>units Protein |
|---|---|---|
| a | 2.1 | 1.2 |
| b | 1.7 | 1.1 |
| c | 1.65 | 1.0 |
| d | 2.0 | 1.2 |
| e | 2.0 | 1.1 |
| pF403 | 1.0 | 1.0 |
| 14007-230-1A<br>(from Example VII) | 1.8 | 1.0 |

*See Example VII

Immunoblot analysis (see Example VII) detected a single major band with a molecular weight of ca. 34-kD. Clone "a" above, hereinafter referred to as Clone 14007-284-1A, was selected for further development.

EXAMPLE IX

Additional Studies of Growth of the S. Cerevisiae (mnn9⁻) Producing preS2+S in Shake Flasks The frozen stock culture 14007-230-1A (Example VII above) was inoculated onto leu⁻ plates containing 1M sorbitol. The plates were incubated inverted at 28° C. for 2 to 3 days. Seed cultures either were established as described in Example VII above or the growth on the plates was resuspended in YEHDS medium, and the resuspended growth was transferred into a 2 liter Erlenmeyer flask containing 500 mL of YEHDS. The flask was incubated at 28° C. and 350 rpm in a controlled environment shaker incubator, for 18–22 hrs.

An inoculum (5% (v/v)) from the seed flask was transferred into a 250 mL or 2 L flask containing 50-mL or 500-mL of YEHDS, respectively. The production flasks then were incubated as described above for 40–46 hrs. An optical density of 8.0 $A_{660}$ units typically was obtained. The cells from the flasks were harvested by centrifuging the contents of the flasks in 500-mL centrifuge bottles for 10 min at 1300 xg. The supernatant was decanted and the cell pellet resuspended in 50–100 mL of a buffered salt solution.

Aliquots (0.6 mL) of 20% washed cell slurries were broken using glass beads (0.45–0.52 mm) in 1.5-mL Eppendorf tubes. PMSF (6.5 ml of 200 mM stock) was added as a protease inhibitor. Aliquots were removed from the tubes after breakage and frozen at −70° C. for immunoblot analysis. Triton X-100 was added to the remaining sample in the tubes to a final concentration of 0.5%, and the samples were briefly mixed and incubated at 4° C. for 20–40 min. The cell debris was removed by centrifugation and the clarified cell extract assayed for preS RIA and Lowry protein.

A typical value obtained was 15.65 mg PreS2+S/mL of fermentation broth and 0.04 mg of preS2+S/mg of total protein.

EXAMPLE X

Large Scale Growth of S. Cerevisiae (mnn9⁻) Producing preS2+S in Fermentors

The frozen stock culture 14007-230-1A was inoculated onto leu⁻ plates containing 1M sorbitol. The plates were incubated inverted at 28° C. for 2–3 days. The growth on the plates was resuspended in YEHDS and the resuspended growth was transferred into 2 L Erlenmeyer flask containing 500 mL of YEHDS. The flask was incubated at 28° C. and 350 rpm in a controlled environment shaker incubator for 18–22 hours. These seed cultures then were used to inoculate the production stage vessels.

An inoculum (1–5% v/v) from one or more flasks was transferred into 16 L or 250 L fermentors containing 10 L or 200 L of YEHDS, respectively. The 16 L fermentors were operated at 500 rpm, 5 L/min air, and 28° C. The 250 L fermentors were operated at 160 RPM, 60 L/min air and 28° C. The fermentors were harvested 40–46 hours after inoculation with the seed culture. Optical density values of 15.0 $A_{660}$ units typically were obtained. Harvesting consisted of concentrating the cells using a hollow fiber filtering device followed by washing the cells in buffered salt solutions. Cell slurries were assayed as described below or stored frozen at −70° C. for further processing and analysis.

Small samples (0.6 mL) of 20% washed cell slurries were broken using glass beads (0.45–0.52 mm) in 1.5 mL Eppendorf tubes. PMSF (6.5 ml of 200 mM stock) was added as a protease inhibitor. Aliquots were removed from the tubes after breakage and frozen at −70° C. for immunoblot analysis. Triton X-100 was added to the remaining sample in the tubes to a final concentration of 0.5%, and the samples were mixed briefly and incubated at 4° C. for 20–40 minutes. The cell debris was removed by centrifugation and the clarified cell extract assayed for preS RIA and Lowry protein. An average value for antigen productivity was 8.4 mg of preS2+S/mL of fermentation broth and 0.025 mg preS2+S protein/mg of total protein.

EXAMPLE XI

The methods of purification of recombinant HBpreS2+S of this invention completely eliminate the formerly requisite introduction of protease inhibitors at any of the purification steps. Yeast cells transformed with expression vectors coding for HBpreS2+S protein or variants thereof are grown and harvested. The cells may be stored if desired, by washing the cells with a buffer solution, e.g. PBS, and forming a cell paste which is typically stored frozen at −70° C.

About 6.6 kg of a frozen yeast cell slurry (producing recombinant preS2+S protein) was thawed and diluted with 1.06 liters of PBS and 7.36 liters of 1M Tris-base buffer, pH 11.0. A crude cell extract was prepared by two passages of the yeast cell suspension through a Gaulin high pressure homogenizer. Following homogenization, TRITON X-100 was added to the crude cell extract (0.1% final concentration). The crude cell extract was heated to 45° C., held at 45°–50° C. for 15 minutes, and then cooled to less than 10° C. using a heat exhanger. After cooling, an aliquot of the heat-treated slurry, representing about 3.25 kg of cells, was diafiltered against 0.1M Tris-base buffer, pH 10.1 containing 0.1% TRITON X-100, using a 0.1 μm–0.2 μm tangential flow, Prostak Durapore (Millipore) membrane, plate and frame diafiltration unit. The volume of the resulting filtrate was 47.8 liters. The filtrate was then concentrated and diafiltered using a hollow fiber diafiltration unit with a molecular weight cutoff of $10^5$, which reduced the volume to about 8.6 liters. The concentrate was then filtered through a dead-end, 0.2 micron pore size filter, and the filtered concentrate was passed through a cartridge containing XAD-4 resin (approximately 320 grams) to remove TRITON X-100. The filtered concentrate was passed through the XAD-4 resin bed at approximately 800 ml/hr (cartridge approximately 3.5 inches in diameter). The PH of the resin treated concentrate was reduced to 7.8 and the extract was applied to a 25 cm×27 cm chromatographic column of wide pore silica, with a pore size range of about 1000 to 1500 angstroms and silica particle size range of about 30 to 130 microns (Amicon), at a flow rate of 5 liters/hr using a peristaltic pump, to absorb the preS2+S protein. The wide pore silica was then washed with 1.5 volumes of PBS (16.8 liters/hr). The preS2+S was eluted from the wide pore silica using 26.25 liters of 50 mM borate buffer, pH 8.7, warmed to 55°–60° C., at a flow rate of 16.8 liters/hr. The preS2+S protein eluate was collected in a volume of 26.25 liters and was then concentrated using a hollow fiber diafiltration unit with a molecular weight cutoff of $10^5$ which reduced the volume to about 1.6 liters. The preS2+S protein was then diafiltered against 50 mM borate buffer, pH 8.7, using a $10^5$ molecular weight cutoff, hollow fiber system.

EXAMPLE XII

About 210 g of frozen yeast cell paste (producing recombinant preS2+S protein) were suspended in about 630 ml of 0.5M TRIS-base buffer, pH 10. A crude cell extract was prepared by 3 passages of the yeast cell suspension through a Stansted high pressure homogenizer. Following homogenization, 43 ml of 10% Triton X-100 was added to the crude yeast cell extract and mixed by gentle stirring. The crude extract was then heated at 55° C. for 30 minutes by immersion in a heated water bath. The extract was then cooled to about 4° C. in an ice water bath. The cooled extract was centrifuged at 3000 xg for 15 minutes at 4° C. The supernatant (clarified extract) was collected in a glass beaker and 155 g of XAD-2 resin was added to remove the Triton X-100. The resin and the clarified extract were gently stirred for about 90 minutes at 2°–8° C. and the resin was removed from the clarified extract by passage through a metal screen. The pH of the extract was then reduced to about 7.6 by adding about 150 ml of 1M HCL. About 230 g of wide pore silica with a pore size of about 1500 angstrom and a particle size of about 100 microns was added to the extract to adsorb the preS2+S protein. The extract and wide pore silica were gently mixed for about 90 minutes at about 2°–8° C. The wide pore silica with preS2+S adsorbed was then washed 5 times with about 6300 ml of PBS at 2°–8° C. The preS2+S protein was eluted from the wide pore silica by adding 1200 ml of 50 mm borate buffer, pH 8.7, at 55° C. Elution was done for about 25 minutes. The elution steps were repeated 3 times. The eluted preS2+S was then concentrated by diafiltration against 50 mM borate buffer, pH 8.7, using a hollow fiber diafiltration unit with a molecular weight cutoff of $10^5$.

EXAMPLE XIII

About 210 g of frozen yeast cell paste (producing recombinant preS2+S protein) were suspended in about 600 ml of 0.5M TRIS-base buffer, pH 10. A crude cell extract was prepared by 3 passages of the yeast cell suspension through a Stansted high pressure homogenizer. Following homogenization, the crude extract was diafiltered against 0.5M TRIS-base buffer, pH 10.4 plus 0.1% Triton X-100 using a 0.1 um–0.2 um tangential flow hollow fiber diafiltration unit. The volume of the resulting filtrate was 7.3 liters. The filtrate was then concentrated by diafiltration using a hollow fiber diafiltration unit with a molecular weight cutoff of $10^5$ which reduced the volume to about 1.3 liters. The concentrate was then heated to about 55° C. for approximately 30 minutes, and cooled to about 2°–8° C. The concentrate was collected in a glass beaker and 250 g of XAD-2 resin was added to remove the TritonX-100. The resin and the concentrated extract were gently stirred for about 90 minutes at 2°–8° C. and the resin was removed from the concentrated extract by passage through a metal screen. After removing the resin, the pH was reduced to 7.7 and the extract was applied to a 5 cm×15 cm chromatographic column of wide pore silica, at a flow rate of 200 ml/hr using a peristaltic pump, to adsorb the preS2+S protein. The wide pore silica was then washed with 9 volumes of PBS (200 ml/hr). The preS2+S was eluted from the wide pore silica using 1400 ml of 50 mm borate buffer, pH 8.7, warmed to 55° C., at a flow rate of 500 ml/hr. The preS2+S protein eluate was collected in a volume of 1.4 liters and was then concentrated using a hollow fiber diafiltration unit with a molecular weight cutoff of $10^5$ which reduced the volume to about 0.48 liters. The preS2+S protein was then diafiltered against 50 mm borate buffer, pH 8.7, using a $10^5$ mw hollow fiber system.

EXAMPLE XIV

About 210 g of frozen yeast cell paste (producing recombinant preS2+S protein) were suspended in about 640 ml of 0.5M TRIS-base buffer, pH 11.3. A crude cell extract was prepared by 3 passages of the yeast cell suspension through a Stansted high pressure homogenizer. Following homogenization, the crude extract was diafiltered against 0.5M TRIS-base buffer, pH 10.4 plus 0.1% TritonX-100 using a 0.1 um–0.2 um tangential flow hollow fiber diafiltration unit. The volume of the resulting filtrate was 7.8 liters. The filtrate was then concentrated by diafiltration using a hollow fiber diafiltration unit with a molecular weight cutoff of $10^5$ which reduced the volume to about 1.1 liters. The concentrate was then heated to about 55° C. for approximately 35 minutes, and cooled to about 8° C. The concentrate was collected in a glass beaker and 285 g of XAD-2 resin was added to remove the TritonX-100. The resin and the concentrated extract were gently stirred for about 90 minutes at 2°–8° C. and the resin was removed from the concentrated extract by passage through a metal screen. After removing the resin, the pH was reduced to 7.7 and the extract was applied to a 5 cm×15 cm chromatographic column of wide pore silica, at a flow rate of 200 ml/hr using a peristaltic pump, to adsorb the preS2+S protein. The wide pore silica was then washed with 9 volumes of PBS (200 ml/hr). The preS2+S was eluted from the wide pore silica using 1200 ml of 50 mm borate buffer, pH 8.7, warmed to 55° C., at a flow rate of 500 ml/hr. The preS2+S protein eluate was collected in a volume of 1.2 liters and was then concentrated using a hollow fiber diafiltration unit with a molecular weight cutoff of $10^5$ which reduced the volume to about 0.43 liters. The preS2+S protein was then diafiltered against 50 mm borate buffer, pH 8.7, using a $10^5$ mw hollow fiber system.

EXAMPLE XV

About 146 g of frozen yeast cell paste (producing recombinant S protein) was suspended in about 800 ml of 0.3M TRIS-base buffer, pH 11.3. A crude cell extract was prepared by two passages of the yeast cell suspension through a Gaulin high pressure homogenizer. Following homogenization, 11 ml of 10% Triton X-100 was added to the crude yeast cell extract and mixed by gentle stirring. The crude extract was then heated at 55° C. for 35 minutes by immersion in a heated water bath. The extract was then cooled to about 4° C. in an ice water bath and centrifuged at 3000 xg for 15 minutes at 4° C. The supernatant (clarified extract) was collected in a glass beaker and 40 g of XAD-2 resin was added to remove the Triton X-100. The resin and the clarified extract were gently stirred for about 3 hours at 2°–8° C. The resin was removed from the clarified extract by passage through cheesecloth. The pH of the extract was then reduced to about 7.2 by adding about 150 ml of 1M HCL. The extract was applied to a 5 cm×15 cm chromatographic column of wide pore silica, at a flow rate of 200 ml/hr using a peristaltic pump, for the purpose of absorbing the S protein. The wide pore silica was then washed with 12 volumes of PBS at a flow rate of 200 ml/hr. The S protein was eluted from the wide pore silica using 630 ml of 50 mM borate buffer, pH 8.7, warmed to 55° C., at a flow rate of 500 ml/hr.

EXAMPLE XVI

About 100 g of frozen yeast cell paste (producing recombinant preS2+S protein) was suspended in about 300 ml of 0.5M TRIS-base buffer, pH 11.5. A crude cell extract was prepared by 3 passages of the yeast cell suspension through a Stansted high pressure homogenizer. Following homogenization, 20 ml of 10% Triton X-100 was added to the crude yeast cell extract and mixed by gentle stirring. The crude extract was centrifuged at 3000 xg for 15 minutes at 4° C. Four sets of samples of the supernatant (clarified extract) were removed following pH adjustment to 10, 9.5, 9.0, 8.5, 8.0, and 7.5. Set I samples were immediately frozen and kept at −70° C. Set II samples were held at 2°–8° C. for 48 hours and then frozen at −70° C. Sets III and IV were heated to 55° C. for 30 minutes. Set III samples were then frozen at −70° C., and set set IV samples were held at 2°–8° C. for 48 hours, then frozen at −70° C.

The amount of preS2+S in all samples was then measured by radio-immuno assay (RIA). Equivalent amounts of preS2+S protein from each sample of each set, were assayed for preS2+S degradation by immunoblot as previously described. PreS2+S in all set I samples remained intact. Samples from set II all contained substantially degraded preS2+S protein. Sets III and IV contained primarily intact preS2+S protein, with little degradation at any pH. The stability of preS2+S protein was substantially enhanced following heat treatment of the samples to 55° C. The samples which were not heat treated demonstrated significant degradation of the preS2+S protein at each pH.

While the forgoing specification teaches the principals of the present invention, with examples provided for the purpose of illustration, it will be understood that the practice of the invention encompasses all of the usual variations, modifications, adaptations, deletions or additions of procedures and protocols described herein, as fall within the scope of the following claims.

EXAMPLE XVII

About 250 g of frozen cell paste (producing recombinant S protein) was resuspended to 17% wet weight/volume (about 1500 ml) in phosphate buffered saline solution (PBS). The cells were heated to 45° C. by immersion in a water bath. The cells were held at 45° C. for 15 minutes and then cooled on ice to about 10° C. The cells were then disrupted by two passages through a Gaulin homogenizer.

Following homogenization, 10% Triton X-100 was added to a final concentration of 0.3% and mixed for about 15 minutes. The cell extract was then centrifuged at 3,600 ×g for 20 minutes at 4° C., and the supernatant was collected.

The superantant was then passaged over a column containing about 200g of XAD-2 resin to remove the Triton X-100. The effluent was then passaged directly over a column containing about 150 g of wide pore silica with a pore size of about 1,500 angstrom and a particle size of about 50 microns. The columns used were 5 cm diameter (Pharmacia) and were run at a flow rate of about 200 ml per hour.

The silica column was washed with PBS until the $A_{280}$ returned to baseline.

The S protein was eluted from the silica column using first, cold borate buffer (50 mM, pH 8.7, 4° C.) at a flow rate of about 500 ml per hour, until a rise in the $A_{280}$ was observed. Once the $A_{280}$ began to rise the column was heated to 55° C. and 55° C. borate buffer was run through the column at about 500 ml per hour. The eluate containing S protein (about 1 L) was collected on ice. The eluate was then concentrated to about 200 ml by difiltration against 50 mM borate buffer at pH 8.7, using a hollow fiber diafiltration unit with a molecular weight cutoff of $10^5$. The S protein was then filtered through a 0.2 micron filter and stored. The product was found to be stable with no significant degradation observed on Western blot analysis.

What is claimed is:

1. A method of substantially purifying recombinant hepatitis B virus surface proteins from a recombinant host extract comprising the steps of:

a) disrupting the host cells in a buffer with a pH of about 9.0 to about 12.0;

b) adjusting the pH to between about 8.5 to 11.0 and heat treating the extract from step (a) to between about 40° C. to about 60° C. followed by cooling to about ambiance;

c) adding detergent to the product of step (b);

d) removing undesired host cellular debris by centrifugation;

e) removing the detergent from the product of step (d);

f) adjusting the pH of the product of step (e) to between about 7.5 to 8.0;

g) subjecting the product of step (f) to wide pore silica beads to adsorb surface protein;

h) eluting the surface protein from the wide pore silica beads;

i) concentrating the eluate of step (h) yielding substantially purified surface protein.

2. A method of substantially purifying recombinant hepatitis B virus surface proteins from a recombinant host cell extract comprising the steps of:

a) disrupting the host cells in a buffer with a pH range of about 9.0 to about 12.0;

b) adjusting the pH to about 10.5 and heat treating the extract of step (a) to between about 40° C. and about 60° C. followed by cooling to about ambiance;

c) adding detergent to the product of step (b);

d) removing undesired host cellular debris by microfiltration;

e) concentration and ultrafiltration of the product of step (d);

f) removing the detergent from the product of step (e);

g) adjusting the pH of the product of step (f) to between about 7.5 to about 7.9;

h) subjecting the product of step (e) to wide pore silica to adsorb surface protein;

i) eluting surface protein from the wide pore silica;

j) concentrating the eluate of step (i) yielding substantially purified surface protein.

3. A method of substantially purifying recombinant hepatitis B virus surface proteins from a recombinant host cell extract comprising the steps of:

a) heating the host cells in a buffer to between about 40° C. and 60° C. followed by cooling to about ambience;

b) disrupting the heat treated cells (a) yielding a crude extract;

c) adding detergent to the product of step (b);

d) removing undesired host cellular debris by centrifugation or microfiltration;

e) concentration or diafiltration of the product of step (d);

f) removing the detergent from the product of step (e) by contacting with a resin which adsorbs detergent;

g) adjusting the pH to between 6.7 and 9.0 and subjecting the product of step (f) to wide pore silica to adsorb surface protein;

(h) eluting the surface protein from the wide pore silica;

(i) concentrating the eluate of step (h) yielding substantially purified surface protein.

4. The method of claim 1 wherein the host cell disruption is conducted in a TRIS buffer of about 0.5 molar at a pH of about 10.5.

5. The method of claim 2 wherein the host cell disruption is conducted in a TRIS buffer of about 0.5 molar at a pH of about 10.5.

6. The method of claim 1 wherein the detergent addition step (c), is omitted.

7. The method of claim 2 wherein the detergent addition step (c), is omitted.

8. The method of claim 2 wherein the microfiltration of step (d) is conducted with a plate and frame microfiltration apparatus with a pore size range of about 0.1μ to about 0.45μ.

9. The method of claim 1 wherein the supernatant of step (d) is concentrated by diafiltration conducted with a hollow fiber diafiltration apparatus with nominal molecular weight of retention of about 100,000.

10. The method of claim 1, step (g) wherein the silica adsorption is conducted using a wide pore silica with a pore size range of about 1,000 to 1,500 angstrom and a silica particle size range of about 30 to 130 microns.

11. The method of claim 2, step (h) wherein the silica adsorption is conducted using a wide pore silica with a pore size range of about 1000 to 1500 angstroms and a silica particle size range of about 30 to 130 microns.

12. The method of claim 1 wherein step (i) is conducted by diafiltration with a hollow fiber diafiltration apparatus with a nominal molecular weight of retention of about 100,000.

13. The method of claim 2 wherein step (j) is conducted by diafiltration with a hollow fiber diafiltration apparatus with a nominal molecular weight of retention of about 100,000.

14. The method of claim 3 wherein the microfiltration of step (d) is conducted with a plate and frame microfiltration apparatus with a pore size range of about 0.1μ to about 0.45μ.

15. The method of claim 3 wherein the product of step (d) is concentrated by diafiltration conducted with a hollow fiber diafiltration apparatus with a nominal molecular weight of retention of about 100,000.

16. The method of claim 3, step (g), wherein the silica adsorption is conducted using a wide pore silica with a pore size range of about 1,000 to 1,500 angstrom, and a silica particle size range of about 30 to 130 microns.

17. The method of claim 3 wherein step (i) is conducted by diafiltration with a hollow fiber diafiltration apparatus with a nominal molecular weight of retention of about 100,000.

18. The method of claim 1 wherein the recombinant host cell is a yeast species.

19. The method of claim 2 wherein the recombinant host cell is a yeast species.

20. The method of claim 3 wherein the recombinant host cell is a yeast species.

* * * * *